US007244608B2

(12) United States Patent
Kim et al.

(10) Patent No.: US 7,244,608 B2
(45) Date of Patent: Jul. 17, 2007

(54) MICROORGANISM PRODUCING 5'-INOSINIC ACID AND PROCESS FOR PRODUCING 5'-INOSINIC ACID USING THE SAME

(75) Inventors: Hyun-Soo Kim, Kyunggi-do (KR); Sung-Oh Chung, Kyunggi-do (KR); Jin-Ho Lee, Kyunggi-do (KR); Sung-Goo Kang, Seoul (KR); Jeong-Hwan Kim, Seoul (KR); Soo-Youn Hwang, Kyunggi-do (KR); Byung-Chon Lee, Seoul (KR); Jae-Chul Lee, Kyunggi-do (KR)

(73) Assignee: Cheil Jedang Corporation, Seoul (KR)

( * ) Notice: Subject to any disclaimer, the term of this patent is extended or adjusted under 35 U.S.C. 154(b) by 419 days.

(21) Appl. No.: 10/227,508

(22) Filed: Aug. 23, 2002

(65) Prior Publication Data

US 2003/0054504 A1   Mar. 20, 2003

Related U.S. Application Data

(63) Continuation of application No. PCT/KR01/02264, filed on Dec. 26, 2001.

(30) Foreign Application Priority Data

Dec. 26, 2000 (KR) ............................... 2000-81471

(51) Int. Cl.
*C12N 1/20* (2006.01)
*C12P 13/04* (2006.01)
(52) U.S. Cl. ................ 435/252.3; 435/106; 435/320.1; 435/193; 435/69.1
(58) Field of Classification Search ...................... None
See application file for complete search history.

(56) References Cited

U.S. PATENT DOCUMENTS 3,762,999 A   10/1973   Nakayama 5,919,670 A   7/1999   Okamoto et al.

FOREIGN PATENT DOCUMENTS

| EP | 0 816 491 A | 1/1998 |
| JP | 2312595 | 12/1990 |
| JP | 5007493 | 1/1993 |
| JP | 11009295 | 12/1998 |

OTHER PUBLICATIONS

*Corynebacterium ammoniagenes*, ATCC 6872, American Type Culture Collection Online Catalog, printed Aug. 14, 2002.
Kawahara Y et al., 1989, "Proline in the Osmoregulation of Brevibacterium lactofermentum" *Agr Bio. Chem.* 53(9):2475-2479.
Collins, 1987, "Transfer of *Brevibacterium ammoniagenes* (Cooke and Keith) to the genus *Corynebacterium* as *Corynebacterium ammoniagenes* comb. nov.", Int. J. Syst. Bacteriol. 37:442-443.
Neuhard J et al., 1987, "Purines and pyrimidines" in *Escherichia coli* and *Salmonella typhimurium*, Ingraham JL and Neidhardt FC, eds., American Society for Microbiology, pp. 445-473.
Reitzer LJ et al., 1987, "Ammonia assimilation and the biosynthesis of glutamine, glutamate, aspartate, asparagine, L-alanine, and D-alanine" in *Escherichia coli* and *Salmonella typhimurium*, Ingraham JL and Neidhardt FC, eds., American Society for Microbiology, pp. 302~320.
Dunlap VJ et al., 1985, "Osmotic regulation of L-proline transport in Salmonella typhimurium" *J. Bacteriol.* 163:296-304.
Balabushevich MI et al., 1983, "Effect of antibiotics on 5'-inosinic acid biosynthesis by a Brevibacterium ammoniagenes mutant" *Prikl. Biokhim. Mikrobiol.* 19(5):590-598.
Teshiba S et al., 1983, "Mechanisms of 5'-inosinic acid accumulation by permeability mutants of Brevibacterium ammoniagenes II: sensitivities of a series of mutants to various drugs" *Agr. Bio. Chem.* 47(5):1035-1041.
Tomita, Kazuhiro et al., 1991, "Stimulation by L-Proline of 5'-Inosinic Acid Production by Mutants of Corynebacterium ammoniagenes," Agric. Biol. Chem. 55 (9), 2221-2225.

*Primary Examiner*—Irene Marx
(74) *Attorney, Agent, or Firm*—Arent Fox LLP

(57) ABSTRACT

The present invention relates to a novel microorganism, *Corynebacterium ammoniagenes* strain CJIP009 having Accession No. KCCM-10226, which is capable of producing 5'-inosinic acid and a process for producing 5'-inosinic acid using the same.

10 Claims, No Drawings

MICROORGANISM PRODUCING 5'-INOSINIC ACID AND PROCESS FOR PRODUCING 5'-INOSINIC ACID USING THE SAME

SPECIFICATION

This application is a continuation application of International Application Serial No. PCT/KR01/02264, filed Dec. 26, 2001 and published in English as WO 02/051984, which claims priority to Korean Application Serial No. 2000/81471, filed Dec. 26, 2000. Said applications are incorporated herein in their entirety by reference.

TECHNICAL FIELD

The present invention relates to a novel microorganism producing 5'-inosinic acid and to a process for producing 5'-inosinic acid using the same.

BACKGROUND

5'-inosinic acid is an intermediate material of the metabolic system of nucleic acid biosynthesis, which is used in a variety of fields, like foods and medicines, and in various kinds of medical areas and is important in animal and plant physiology. In particular, 5'-inosinic acid is a nucleic acid-type seasoning that has synergic effect when used with sodium glutamate.

Processes for producing 5'-inosinic acid by direct fermentation have been known in this field, and the important key in economical aspects was to produce 5'-inosinic acid in a high concentration and yield.

DISCLOSURE OF THE INVENTION

The present inventors conducted extensive studies to develop a new strain capable of achieving the above mentioned purposes, and as a result, discovered a novel microorganism producing 5'-inosinic acid by direct fermentation in a high concentration and yield.

The present invention provides a mutant of *Corynebacterium ammoniagenes* CJIP009 (Accession Number KCCM-10226) that is characterized by accumulating 5'-inosinic acid in a high concentration and yield by direct fermentation and having resistance to L-glutamine analogues selected from Azaserine or 6-diazo-5-oxo-L-norleucine (DON), and resistance to L-proline analogues selected from 3,4-dehydroproline, L-azetidine-2-carboxylic acid, L-thiazolidine-4-carboxylic acid, (S)-2,2-dimethyl-4-oxazolidecarboxylic acid, (S)-5,5-dimethyl-4-thiazolide carboxylic acid, (4S,2RS)-2-ethyl-4-thiazoline-carboxylic acid, (2S,4S)-4-hydroxy-2-pyrroline-carboxylic acid, 2-piperidinecarboxylic acid or 2,5-pyrrolidinedione.

The present invention also provides a process for producing 5'-inosinic acid characterized by cultivating the mutant of *Corynebacterium ammoniagenes* CJIP009 (KCCM-10226) followed by collection of the cultivated substances.

The artisan of ordinary skill will recognize that *Corynebacterium ammoniagenes* was formerly called *Brevibacterium ammoniagenes*. See e.g. Collins, 1987, "Transfer of *Brevibacterium ammoniagenes* (Cooke and Keith) to the genus *Corynebacterium* as *Corynebacterium ammoniagenes* comb. nov.", Int. J. Syst. Bacteriol. 37:442–443.

The microorganism of the present invention, a mutant of *Corynebacterium ammoniagenes* (ATCC-6872), requires Adenine, but does not require Xanthine or Guanine. However, growth of the mutant microorganism of the invention is facilitated by adding Xanthine or Guanine, when compared with a conventional Adenine Leaky Mutant producing 5'-inosinic acid [Agr. Bio. Chem., Vol. 47(5), pp. 1035–1041, 1983, (KY13102, KY13171, KY13184, etc.)] The mutant microorganism of the invention may simultaneously require Adenine and Xanthine or Guanine.

In addition, the microorganism of the present invention lacks Urease to assimilate Urea, and has a high sensitivity to lysozyme, the cell wall degrading enzyme, which is considered that the capacity of cell wall synthesis is partially lost, so that lots of intracellularly produced 5'-inosinic acid is easily secreted out of the cell. According to the invention, a microorganism is sensitive to lysozyme if the minimum inhibitory concentration is equal to or less than 8.0 μg/mL.

Balabushevich, M. I. and Kazarinova, L. A., et al (Prikl. Biokhim. Mikrobiol., 19(5), 590–598, 1983), Russia, discovered that adding streptomycin and kanamycin to the medium enhanced cell wall permeability and helps accumulation of 5'-inosinic acid in the medium. Considering this, it was hypothesized that a mutant, capable of producing 5'-inosinic acid in a high concentration and yield, would have been discovered by introducing resistance of streptomycin to a known strain to enhance the membrane permeability of the microorganism. Then, it was further hypothesized that the contamination frequently occurring in fermentation would be prevented by using the above mutant and adding the streptomycin to the medium. Therefore, the present inventors obtained a strain having resistance to a high concentration of streptomycin and studied properties of the strain. In practice, it was determined that strains having resistance to high concentrations of streptomycin may be grown without contamination occurring during fermentation.

Most bacteria accumulate calcium ions and organic solutes, i.e., osmolytes, by improving intracellular osmotic pressure of bacteria to prevent osmotic dehydration under extracellular osmotic pressure of bacteria. Such osmolytes include L-proline, L-glutamate, sugar, N-methylated amino acid derivatives, etc. Among these, L-proline has been known as an important factor of osmoregulation. It has been reported that intracellular L-proline accumulated in *Brevibacterium typhimurium* by increasing the activity of pyrroline-5-carboxylate reductase, which is the important enzyme of biosynthesis pathway of proline when the extracellular concentration of 5'-inosinic acid increased [Agr, Bio, Chem., Vol. 53(9), pp. 2475–2479, 1989]. In addition, it was reported that extracellular osmotic pressure induced intracellular accumulation of L-proline in *Escherichia coli, Salmonella typhimurium, Serratia marcescens*, and others [J, Bacteriol., Vole 163, p 296, 1985].

Accordingly, it is contemplated that in order to have a microorganism capable of producing 5'-inosinic acid in a high concentration and yield, it is important to prevent the inhibition of growth and biochemical metabolic process by increasing intracellular L-proline synthesis and that it is important to reinforce the osmotic pressure-resistant characteristics by enhancing the synthetic capacity of L-proline.

Further, in order to produce 5'-inosinic acid from 5-phosphoribosyl-α-1-pyrophosphate (PRPP), i.e., a purine-type nucleic acid precursor, 2 molecules of glutamine are needed. Glutamine synthetase, which produces glutamine from sodium glutamate, is very elaborately regulated by amino acids, such as glycine, alanine, histidine, etc., and CTP, AMP, etc. [*Escherichia coli* and *Salmonella typhimurium*, 1987, p 302~320]. Therefore, a harmonious supply of glutamine is necessary for the synthesis of 5'-inosinic acid.

Further, produced glutamine is widely used as a precursor of various reactions. In the synthesis of 5'-inosinic acid, two enzymes, which are PRPP amidotransferase and 5-phosphoribosyl-N-formylglycinamide (FGAR) amidotransferase, employ glutamine as a substrate [*Escherichia coli* and *Salmonella typhimurium*, 1987, pp. 445–473]. Therefore, in order to more effectively achieve 5'-inosinic acid synthesis, it is considered that the harmonious synthesis of glutamine is important to increase the affinity of PRPP amidotransferase and FGAR amidotransferase related to synthesis of 5'-inosinic acid to the glutamine rather than other enzymes among various reaction requiring glutamine.

Accordingly, the present inventors tested the effect of various amino acids on the synthesis of 5'-inosinic acid by direct fermentation. As the result, the inventors determined that the fermentation concentration of 5'-inosinic acid increased upon addition of L-glutamine to the medium. The inventors further determined that the appropriate supply of L-glutamine to the present strain is a rate-limiting step in the synthesis of 5'-inosinic acid.

The inventors identified that the microorganisms introduced resistance to L-glutamine analogues, such as Azaserine or 6-diazo-5-oxo-L-norleucine (DON), and resistance to various L-proline analogues, such as 3,4-dehydroproline, L-azetidine-2-carboxylic acid, L-thiazolidine-4-carboxylic acid, (S)-2,2-dimethyl-4-oxazolidecarboxylic acid, (S)-5,5-dimethyl-4-thiazolide carboxylic acid, (4S,2RS)-2-ethyl-4-thiazoline-carboxylic acid, (2S,4S)-4-hydroxy-2-pyrroline-carboxylic acid, 2-piperidinecarboxylic acid or 2,5-pyrrolidinedione can produce 5'-inosinic acid by direct fermentation method in a higher concentration and yield than the known strains. The present invention is based on such discovery.

The microorganism of the present invention, a mutant of *Corynebacterium ammoniagenes* (ATCC-6872), requires Adenine, but does not require Xanthine or Guanine, though the growth is facilitated by adding them. In addition, the microorganism lacks Urease to assimilate Urea and is highly sensitive to lysozyme. Without being restricted to a particular model, it is believed that the mutant microorganism of the invention is partially deficient in cell wall synthesis, a property which may promote secretion of intracellularly produced 5'-inosinic acid. The microorganism of the invention may be resistant to streptomycin, particularly high concentrations of streptomycin.

A high concentration of glucose or other carbon sources added during the culture period and 5'-inosinic acid accumulated during the later culture period lead to an increase in extracellular osmotic pressure of 5'-inosinic acid-producing microorganisms thereby inhibiting their normal physiological activities and cell growth. Therefore, it is desirable to improve the osmotic resistance to prevent the reduction of 5'-inosinic acid production.

To increase the intracellular concentration of proline which plays an important role in osmoregulation to a high accumulation of solutes in the extracellular environment, the microorganism of the present invention has resistance to L-proline analogues, such as 3,4-dehydroproline, L-azetidine-2-carboxylic acid, L-thiazolidine-4-carboxylic acid, (S)-2,2-dimethyl-4-oxazolidecarboxylic acid, (S)-5,5-dimethyl-4-thiazolide carboxylic acid, (4S,2RS)-2-ethyl-4-thiazoline-carboxylic acid, (2S,4S)-4-hydroxy-2-pyrroline-carboxylic acid, 2-piperidinecarboxylic acid or 2,5-pyrrolidinedione, thereby excluding the effect of osmotic pressure more efficiently.

Further, the microorganism of the present invention has resistance to L-glutamine analogues, such as Azaserine or 6-diazo-5-oxo-L-norleucine (DON), essentially required in the purine-type synthesis system by achieving the harmonious supply of glutamine for the synthesis of 5'-inosinic acid, resulting in directly accumulating 5'-inosinic acid in a high yield and concentration.

The protocol by which the mutant microorganims of the present invention was isolated began with strain CJ 12 as the parental strain and consisted of several iterations of mutagenesis and screening. In each iteration, microorganisms were treated with X-ray irradiation, ultraviolet ray irradiation, and/or a chemical mutagen, such as N-methyl-N'-nitro-N-nitrosoguanidine (NTG), diethyl sulfate, ethyl amine, etc., and then screened for 5'-inosinic acid production. Treated bacteria were suitably suspended and spread on a minimal medium (Medium 2) containing 1.7% agar and each concentration of variants. Then, each colony was cultivated on a nutrition medium (Medium 1) followed by a seed medium (Medium 3) for 24 hours and a fermentation medium (Medium 4) for 5–6 days. Colonies that produced the highest levels of 5'-inosinic acid were selected for subsequent rounds of mutagenesis.

After several iterations this mutagenesis protocol, the inventors isolated the microorganism of the present invention, which produces high levels of 5'-inosinic acid, lacks Urease, is sensitive to lysozyme, is resistant to L-glutamine, L-proline, and high concentrations of streptomycin, and requires Adenine, but does not require Xanthine or Guanine, though growth is facilitated by adding them, and lacks Urease to assimilate Urea. This strain was designated CJIP009. *Corynebacterium ammoniagenes* CJIP009 was deposited under the Budapest Treaty to the Korean Culture Center of Microorganisms whose address is 361-221 Yurin B/D Hongje-1-dong, Seodaemun-gu, Seoul 120-091, on Nov. 15, 2000 and assigned Accession No. KCCM-10226.

Specifically, the present invention provides a process for producing 5'-inosinic acid by cultivating *Corynebacterium ammoniagenes* strain CJIP009 (KCCM-10226) on a seed medium at 30° C. for 24 hours, cultivated and activated on a fermentor seed medium at 28–34° C., 900 rpm and pH 7.2 for 1–2 days, cultivated on a fermentor main medium at 30° C., 900 rpm and pH 7.2 for 5–6 days. When reducing sugars are present in the culture solution at a concentration of 2% (w/v), a mixture of fructose, glucose, and molasses was added four times until the final concentration of reducing sugars in the culture solution was increased to 32% (w/v).

Culture media employed in the present invention have the following compositions:

Medium 1: Nutrition Medium peptone 1%, Beef extract 1%, Sodium Chloride (NaCl) 0.25°/a, Yeast Extract 1%, Agar 2%, pH 7.2

Medium 2: Minimal Medium

Glucose 2.0%, Ammonium Sulfate ($(NH4)_2SO_4$) 0.3%, Potassium Dihydrogen Phosphate ($KH_2PO_4$) 0.1%, Potassium Monohydrogen Phosphate ($K_2HPO_4$) 0.3%, Magnesium Sulfate ($MgSO_4\cdot 7H_2O$) 0.3%, Calcium chloride ($CaCl_2$) 10 mg/L, Ferric Sulfate ($FeSO_4\cdot 7H_2O$) 10 mg/L, Zinc Sulfate ($ZnSO_4\cdot 7H_2O$) 1.0 mg/L, Manganese Chloride ($MnCl_2\cdot H_2O$) 3.6 mg/L, L-Cystein 20 mg/L Calcium Pantothenate 10 mg/L, Thiamine.HCl 5.0 mg/L, Biotin 30 μg/L, Adenine 20 mg/L, Guanine 20 mg/L, pH 7.3

Medium 3: Seed Medium

Glucose 5%, peptone 0.5%, Beef extract 0.5%, Yeast Extract 1%, Sodium Chloride (NaCl) 0.25%, Adenine 100 mg/L, Guanine 100 mg/L, pH 7.2

Medium 4: Flask Fermentation Medium

Sodium Glutamate 01%, Ammonium Chloride ($NH_4Cl$) 1.0%, Magnesium Sulfate ($MgSO_4\cdot 7H_2O$) 1.2%, Calcium Chloride ($CaCl_2$) 0.01%, Ferric Sulfate ($FeSO_4.7H_2O$) 20 mg/L, Manganese Sulfate ($MnSO_4.H_2O$) 20 mg/L, Zinc Sulfate ($ZnSO_4.7H_2O$) 20 mg/L, Cupric Sulfate ($CuSO_4.7H_2O$) 5.0 mg/L, L-Cystein 23 mg/L, Alamne 24 mg/L, Nicotinic acid 8.0 mg/L, Biotin 45 µg/L, Thiamine.HCl 5.0 mg/L, Adenine 30 mg/L, phosphoric acid ($H_3PO_4$) (85%) 1.9%, the mixture of Fructose, Glucose and molasses to 8% (w/v) as reducing sugar (pH 7.2).

Medium 5: Fermentator Seed Medium

Glucose 5.4%, peptone 1.0%, Yeast Extract 2.0%, Potassium Dihydrogen Phosphate ($KH_2PO_4$) 0.1%, Potassium Monohydrogen Phosphate ($K_2HPO_4$) 0.1%, Magnesium Sulfate ($MgSO_4.7H_2O$) 0.1%, Ammonium Sulfate (($NH4)_2SO_4$) 0.5%, Ferric Sulfate ($FeSO_4.7H_2O$) 80 mg/L, Zinc Sulfate ($ZnSO_4$ 7H20) 40 mg/L, Manganese Sulfate ($MnSO_4.H_2O$) 40 mg/L, L-Cystein 80 mg/L, Calcium Pantothenate 60 mg/L, Thiamine-HCl 20 mg/L, Biotin 240 µg/L, Adenine 1200 mg/L, Guanine 1200 mg/L (pH 7.2).

Medium 6: Fermentor Main Medium

Calcium Chloride ($CaCl_2$) 120 mg/L, Cupric Sulfate ($CuSO_4.7H_2O$) 8.0 mg/L, Magnesium Sulfate ($MgSO_4.7H_2O$) 1.5%, Ferric Sulfate ($FeSO_4.7H_2O$) 24 mg/L, Zinc Sulfate ($ZnSO_4.7H_2O$) 24 mg/L, Manganese Sulfate ($MnSO_4.H_2O$) 24 mg/L, L-Cystein 26.4 mg/L, Sodium Glutamate 0.12%, Thiamine.HCl 6.0 mg/L, Biotin 40 µg/L, Nicotinic acid 50 mg/L, Alanine 145 mg/L, Adenine 200 mg/L, phosphoric acid ($H_3PO_4$)(85%) 4.3%, the mixture of Fructose, Glucose and molasses to 32% as reducing sugar (pH 7.2)

The biochemical properties of representative variants of the novel strain CJIP009 according to the present invention is shown in the following Table 1 (This invention is not limited to the following properties).

TABLE 1

| Property | ATCC6872 | CJIP009 (KCCM-10226) |
|---|---|---|
| Adenine | Not require | Require |
| Guanine (Xanthine) | Not require | Leaky |
| Sensitivity to lysozyme (minimal growth inhibition concentration) | 80 µg/ml | 8 µg/ml |
| Resistance to 3,4-dehydroproline | 1,000 µg/ml | 3,500 µg/ml |
| Streptomycin | 500 µg/ml | 2,000 µg/ml |
| L-azetidine-2-carboxylic acid | 5 mg/ml | 30 mg/ml |
| L-thiazolidine-4-carboxylic acid | 10 µg/ml | 100 µg/ml |
| Azaserine | 25 µg/ml | 100 µg/ml |

The culture process of 5'-inosinic acid used in the invention was as follows.

The microorganisms, belonging to *Corynebacterium* genus and capable of producing 5'-inosinic acid, were cultured in conventional medium containing carbon sources, nitrogen sources, amino acids, vitamins, etc., under aerobic condition with regulated temperature, pH, etc.

Glucose, fructose, sterilized pre-treated molasses (molasses reverted to reducing sugar) and so on, would be used as a carbon source. Among inorganic nitrogen sources such as, ammonia, ammonium chloride, ammonium sulfate and organic nitrogen sources such as, peptone, NZ-amine, meat extract, yeast extract, corn digestive solution, casein hydrolysate, fishes or degradation products thereof, defatted soybean cake or degradation products thereof and so on, each would be used as a organic nitrogen source. Potassium Dihydrogen Phosphate ($KH_2PO_4$), Potassium Monohydrogen Phosphate ($K_2HPO_4$), Manganese Sulfate ($MnSO_4.H_2O$), Ferric Sulfate ($FeSO_4.7H_2O$), Magnesium Sulfate ($MgSO_4$ $7H_2O$), Calcium Carbonate ($CaCO_3$), etc., would be used as the inorganic compounds. If required, vitamins and base, etc., would be added. The culture is performed for example, while shaking or aerating and agitating under aerobic condition, preferably at 20–40° C. for 5~6 days. The pH of the medium preferably remains around neutrality. The 5'-inosinic acid accumulated by direct fermentation is analyzed by the conventional method.

BEST MODE FOR CARRYING OUT THE INVENTION

This invention will be better understood from the following examples. However, one skilled in the art will readily appreciate the specific materials and the results described below are merely illustrative of, and are not intended to, nor should be intended to, limit the invention as described more fully in the claims which follows thereafter.

EXAMPLE 1

Selection of Microorganism Sensitive to Lysozyme (LY002)

*Corynebacterium ammoniagenes* strain CJ112 (ATCC-6872), the parent strain, was suspended to $10^7$~$10^8$ cells/mL in the phosphate buffer (pH 7.0) or citrate buffer (pH 5.5). N-methyl-N'-nitro-N-nitrosoguanidine (NTG) was added to a final concentration of 10~50 µg/mL at room temperature or 32° C. After 20~40 minutes, cells were washed twice with 0.85% saline. Colonies were obtained by suitably suspending and spreading cells on a minimal medium (Medium 2) containing 1.7% agar. Then, each colony was tooth picked on to the minimal medium (Medium 2) containing 1.7% agar and on the minimal medium (Medium 2) containing 1.7% agar and 40 pg/mL of lysozyme. First, microorganisms that grew on the minimal medium containing 1.7% agar, but not on the minimal medium containing 40 µg/mL of lysozyme were selected. The microorganism was to be a parent strain and to be continuously induced in the above mutation. In a second screen, microorganisms that did not grow on the minimal medium containing 16 µg/mL lysozyme were selected. Finally, according to the above method, microorganisms that did not grow on the minimal medium containing 8 µg/mL of lysozyme were selected. The colony of highly lysozyme sensitive microorganisms was cultivated on a nutrition medium (Medium 1), then cultivated for 24 hours on a seed medium (Medium 3), and cultivated for 3~4 days on a culture medium (Medium 4) thereby to select LY002 that can produce 5'-inosinic acid accumulated in the culture medium at the largest amounts. The concentration of lysozyme, at which the microorganism shows sensitivity, is listed in Table 2.

TABLE 2

|  | CJ112 | LY002 |
|---|---|---|
| Concentration of lysozyme | 80 µg/ml | 8 µg/ml |

EXAMPLE 2

Selection of Streptomycin-resistant Strain (CISM10)

The mutant of Example 1, strain LY002, was used as the parent strain for Example 2. LY002 was suspended to $10^7$~$10^8$ cells/mL in the phosphate buffer (pH 7.0) or citrate buffer (pH 5.5). NTG mutagenesis was performed as in Example 1. Colonies were obtained by suitably suspending and spreading cells on a 3 minimal media (Medium 2), which contained 1.7% agar and 1,000 μg/ml, 1,500 μg/mL or 2,000μg/mL of streptomycin, respectively. Then, each colony was cultivated on the nutrition medium (Medium 1), then cultivated for 24 hours on a seed medium (Medium 3), and cultivated for 3~4 days on a culture medium (Medium 4) thereby to select CISM10 that can produce 5'-inosinic acid accumulated in the culture medium at the largest amounts. The concentration of streptomycin, at which the microorganism shows resistance, is listed in Table 3.

TABLE 3

|  | LY002 | CISM10 |
|---|---|---|
| Concentration of streptomycin | 500 μg/ml | 2,000 μg/ml |

EXAMPLE 3

Selection of 3,4-dehydroproline-resistant Strain (CS101)

The mutant of Example 2, strain CISM10, was used as the parent strain for Example 3. CISM10 was suspended to $10^7$~$10^8$ cells/mL in the phosphate buffer (pH 7.0) or citrate buffer (pH 5.5). NTG mutagenesis was performed as in Example 1. Colonies were obtained by suitably suspending and spreading cells on a 3 minimal media (Medium 2), which contained 1.7% agar and 1,500 μg/ml, 2,500 μg/ml, or 3,500 μg/mL of 3,4-dehydroproline, respectively. Then, each colony was cultivated on the nutrition medium (Medium 1), then cultivated for 24 hours on a seed medium (Medium 3), and cultivated for 3–4 days on a culture medium (Medium 4) thereby to select CIS104 that can produce 5'-inosinic acid accumulated in the culture medium at the largest amounts. The concentration of 3,4-dehydroproline, at which the microorganism shows resistance, is listed in Table 4.

TABLE 4

|  | CISM10 | CS101 |
|---|---|---|
| Concentration of 3,4-dehydroproline | 1,000 μg/ml | 3,500 μg/ml |

EXAMPLE 4

Selection of L-azetidine-2-carboxylic Acid-resistant Strain (CIAC12)

The mutant of Example 3, strain CS101, was used as the parent strain for Example 4. CS101 was suspended to $10^7$~$10^8$ cells/mL in the phosphate buffer (pH 7.0) or citrate buffer (pH 5.5). NTG muta genesis was performed as in Example 1. Colonies were obtained by suitably suspending and spreading cells on a 3 minimal media (Medium 2), which contained 1.7% agar and 10 μg/ml, 20 μg/ml, or 30 μg/mL of L-azetidine-2-carboxylic acid, respectively. Then, each colony was cultivated on the nutrition medium (Medium 1), then cultivated for 24 hours on a seed medium (Medium 3), and cultivated for 3~4 days on a culture medium (Medium 4), thereby to select CIAC12 that can produce 5'-inosinic acid accumulated in the culture medium at the largest amounts. The concentration of L-azetidine-2-carboxylic acid, at which the microorganism shows resistance, is listed in Table 5.

TABLE 5

| Property | CISM10 | CIAC12 |
|---|---|---|
| Concentration of L-azetidine-2-carboxylic acid | 5 mg/ml | 30 mg/ml |

EXAMPLE 5

Selection of L-thiazolidine-4-carboxylic Acid-resistant Strain (CITP13)

The mutant of Example 4, strain CIAC12, was used as the parent strain for Example 5. CIAC12 was suspended to $10^7$~$10^8$ cells/mL in the phosphate buffer (pH 7.0) or citrate buffer (pH 5.5). NTG mutagenesis was performed as in Example 1. Colonies were obtained by suitably suspending and spreading cells on a 3 minimal media (Medium 2), which contained 1.7% agar and 20 μg/ml, 50 μg/ml, or 100 μg/mL of L-thiazolidine-4-carboxylic acid, respectively. Then, each colony was cultivated on the nutrition medium (Medium 1), then cultivated for 24 hours on a seed medium (Medium 3), and, cultivated for 3~4 days on a culture medium (Medium 4) thereby to select CITP13 that can produce 5'-inosinic acid accumulated in the culture medium at the largest amounts. The concentration of L-thiazolidine-4-carboxylic acid, at which the microorganism shows resistance, is listed in Table 6.

TABLE 6

|  | CISM10 | CS101 |
|---|---|---|
| Concentration of L-thiazolidine-4-carboxylic acid | 10 μg/ml | 100 μg/ml |

EXAMPLE 6

Selection of Azaserine-resistant Strain CJIP009 (KCCM-10226)

The mutant of Example 5, strain CITP13, was used as the parent strain for Example 6. CITP13 was suspended to $10^7$~$10^8$ cells/mL in the phosphate buffer (pH 7.0) or citrate buffer (pH 5.5). NTG mutagenesis was performed as in Example 1. Colonies were obtained by suitably suspending and spreading cells on a 3 minimal media (Medium 2), which contained 1.7% agar and 50 μg/ml, 75 μg/ml, or 100 μg/mL of azaserine, respectively. Then, each colony was cultivated on the nutrition medium (Medium 1), then cultivated for 24 hours on a seed medium (Medium 3), and cultivated for 3–4 days on a culture medium (Medium 4) thereby to select CJIP009 (KCCM-10226) that can produce 5'-inosinic acid accumulated in the culture medium at the largest amounts. The concentration of azaserine, at which the microorganism shows resistance, is listed in Table 7.

TABLE 7

|  | CITP13 | CJIP009 (KCCM-10226) |
|---|---|---|
| Concentration of azaserine | 25 μg/ml | 100 μg/ml |

EXAMPLE 7

Measurement of the Accumulation Amount of 5'-Inosinic Acid in a Smaller Scale Culture Strain:
CJIP009 (KCCM-10226)
Seed Medium:
Glucose 5%, peptone 0.5%, Beef extract 0.5%, Yeast Extract 1%, Sodium Chloride (NaCl) 0.25%, Adenine 100 mg/L, Guanine 100 mg/L, pH 7.2.

Flask Fermentation Medium:
Sodium Glutamate 0.1%, Ammonium Chloride ($NH_4Cl$) 1.0%, Magnesium Sulfate ($MgSO_4.7H_2O$) 1.2%, Calcium Chloride ($CaCl_2$) 0.01%, Ferric Sulfate ($FeSO_4.7H_2O$) 20 mg/L, Manganese Sulfate ($MnSO_4.H_2O$) 20 mg/L, Zinc Sulfate ($ZnSO_4\ 7H_2O$) 20 mg/L, Cupric Sulfate ($CuSO_4\ 7H_2O$) 5.0 mg/L, L-Cystein 23 mg/L, Alanine 24 mg/L, Nicotinic acid 8.0 mg/L, .Biotin 45 µg/L, Thiamine-HCl 5.0 mg/L, Adenine 30 mg/L, phosphoric acid ($H_3PO_4$)(85%) 1.9%, the mixture of Fructose, Glucose and molasses to 8% as reducing sugar (pH 7.2)

Fermentation Procedure:
3 mL of the seed medium was introduced into a test tube of 18 mm diameter and sterilized under elevated pressure by known methods. Strain CJIP009 was inoculated into the sterilized medium and cultivated while shaking at 30° C. for 24 hours to use as the seed medium. 27 mL of fermentation medium was introduced into 500 mL of Erlenmeyer flask for shaking and sterilized under elevated pressure at 120° C. for 10 minutes. 3 mL of seed culture was then inoculated and cultivated for 5~6 days. The flask was shaken at 200 rpm at the temperature of 30° C. and pH of 7.2.

The amount of 5'-inosinic acid that accumulated was 19.1 g/L.

EXAMPLE 8

Measurement of the Accumulation Amount of 5'-Inosinic Acid in a Larger Scale Culture Strain:
CJIP009 (KCCM-10226)
Seed medium: same as example 7
Fermentor Seed Medium Glucose 5.4%, peptone 1.0%, Yeast Extract 2.0%, Potassium Dihydrogen Phosphate ($KH_2PO_4$) 0.1%, Potassium Monohydrogen Phosphate ($K_2HPO_4$) 0.1%, Magnesium Sulfate ($MgSO_4.7H_2O$) 0.1%, Ammonium Sulfate (($NH4$)$_2SO_4$) 0.5%, Ferric Sulfate ($FeSO_4.7H_2O$) 80 mg/L, Zinc Sulfate ($ZnSO_4.7H_2O$) 40 mg/L, Manganese Sulfate ($MnSO_4.H_2O$) 40 mg/L, L-Cystein 80 mg/L Calcium Pantothenate 60 mg/L, Thiamine-HCl 20 mg/L, Biotin 240 µg/L, Adenine 1200 mg/L, Guanine 1200 mg/l (pH 7.2)

Fermentor Main Medium
Calcium Chloride ($CaCl_2$) 120 mg/L, Cupric Sulfate ($CuSO_{4-7}H_2O$) 8.0 mg/L, Magnesium Sulfate ($MgSO_4.7H_2O$) 1.5%, Ferric Sulfate ($FeSO_4.7H_2O$) 24 mg/L, Zinc Sulfate ($ZnSO_4.7H_2O$) 24 mg/L, Manganese Sulfate ($MnSO_4-H_2O$) 24 mg/L, L-Cystein 26.4 mg/L, Sodium Glutamate 0.12%, Thiamine-HCl 6.0 mg/L, Biotin 40 µg/L, Nicotinic acid 50 mg/L, Alanine 145 mg/L, Adenine 200 mg/L, phosphoric acid ($H_3PO_4$)(85%) 4.3%, the mixture of Fructose, Glucose and molasses to 32% as reducing sugar (pH 7.2)

Fermentation Procedure:
50 mL of the seed medium was introduced into 500 mL of Erlenmeyer flask for shaking and sterilized under elevated pressure by the general method. Strain CJIP009 was inoculated on the seed medium and cultivated while shaking at 30° C. for 24 hours. The culture solution obtained was used as a seed culture.

A liter (1000 mL) of seed medium was sterilized in a 2.5 L fermentor under elevated pressure at 120° C. for 15 minutes. This medium was inoculated with 50 mL of the above seed culture and cultivated for 1~2 days while shaking at 900 rpm at the temperature of 28~34° C. at a pH of 7.2. The culture solution obtained was used as a main culture.

A 5 L fermentor was filled with 1,250 mL of fermentor main medium and sterilized under elevated pressure at 120° C. for 15 minutes. This medium was inoculated with 250 mL of the above main culture and cultivated. When reducing sugars were present in the medium at a concentration of 2%, a mixture of Fructose, glucose, and molasses was added four times until the final concentration of reducing sugars in the culture solution was increased to 32% (w/v). After a reducing sugar concentration of 32% was achieved, the culture was cultivated for 5–6 days while shaking at 900 rpm at the temperature of 30° C. and a pH of 7.2.

The amount of 5'-inosinic acid that accumulated in the medium was 70.3 g/L.

INDUSTRIAL APPLICABILITY

According to the present invention, 5'-inosinic acid can be obtained in a higher concentration and yield than in the prior art. According to the present invention, 5'-inosinic acid can be obtained more economically than in the prior art.

What is claimed is:

1. Isolated *Corynebacterium ammoniagenes* strain CJIP009 having Accession No. KCCM-10226.

2. The isolated *Corynebacterium ammoniagenes* strain CJIP009 of claim 1, wherein said strain is resistant to a L-glutamine analog selected from the group consisting of azaserine and 6-diazo-5-oxo-L-norleucine (DON).

3. The isolated *Corynebacterium ammoniagenes* strain CJIP009 of claim 1, wherein said strain is resistant to a L-proline analog selected from the group consisting of 3,4-dehydroproline, L-azetidine-2-carboxylic acid, L-thiazolidine-4-carboxylic acid, (S)-2,2-dimethyl-4-oxazolidecarboxylic acid, (S)-5,5-dimethyl-4-thiazolide carboxylic acid, (4S,2RS)-2-ethyl-4-thiazoline-carboxylic acid, (2S, 4S)-4-hydroxy-2-pyrroline-carboxylic acid, 2-piperidinecarboxylic acid, and 2,5-pyrrolidinedione.

4. The isolated *Corynebacterium ammoniagenes* strain CJIP009 of claim 1, wherein said strain is resistant to a L-glutamine analog selected from the group consisting of azaserine and 6-diazo-5-oxo-L-norleucine (DON) and resistant to a L-proline analog selected from the group consisting of 3,4-dehydroproline, L-azetidine-2-carboxylic acid, L-thiazolidine-4-carboxylic acid, (S)-2,2-dimethyl-4-oxazolidecarboxylic acid, (S)-5,5-dimethyl-4-thiazolide carboxylic acid, (4S,2RS)-2-ethyl-4-thiazoline-carboxylic acid, (2S,4S)-4-hydroxy-2-pyrroline-carboxylic acid, 2-piperidinecarboxylic acid, and 2,5-pyrrolidinedione.

5. The isolated *Corynebacterium ammoniagenes* strain CJIP009 of claim 1, wherein said strain may be resistant to streptomycin.

6. The isolated *Corynebacterium ammoniagenes* strain CJIP009 of claim 1, wherein said strain requires exogenous adenine.

7. The isolated *Corynebacterium ammoniagenes* strain CJIP009 of claim 1, wherein said strain is guanine or xanthine leaky.

8. The isolated *Corynebacterium ammoniagenes* strain CJIP009 of claim 1, wherein said strain is sensitive to about 8 μg/mL lysozyme.

9. A process for producing 5'-inosinic acid comprising:
cultivating *Corynebacterium ammoniagenes* strain CJIP009 having Accession No. KCCM-10226 under conditions that allow 5'-inosinic acid to be produced, wherein a fermented culture media is formed and 5'-inosinic acid is produced.

10. The process of claim 9 further comprising isolating 5'-inosinic acid from the fermented culture media.

* * * * *